US005567627A

United States Patent [19]

Lehnen

[11] Patent Number: 5,567,627
[45] Date of Patent: * Oct. 22, 1996

[54] METHOD AND COMPOSITION FOR THE SIMULTANEOUS AND DISCRETE ANALYSIS OF MULTIPLE ANALYTES

[75] Inventor: Brian C. Lehnen, San Carlos, Calif.

[73] Assignee: Trans-Med Biotech, Incorporated, S. South Francisco, Calif.

[*] Notice: The portion of the term of this patent subsequent to Sep. 23, 2012, has been disclaimed.

[21] Appl. No.: 149,129

[22] Filed: Nov. 5, 1993

Related U.S. Application Data

[63] Continuation of Ser. No. 731,039, Jul. 16, 1991, abandoned.

[51] Int. Cl.$^6$ .................. G01N 33/543; G01N 33/546
[52] U.S. Cl. .................. 436/518; 435/973; 435/974; 436/164; 436/172; 436/523; 436/531; 436/534; 436/536; 436/538; 436/541; 436/805
[58] Field of Search .................. 435/973, 974; 436/10, 164, 172, 518, 523, 531, 534, 536–538, 541, 805, 811

[56] References Cited

U.S. PATENT DOCUMENTS

| | | | |
|---|---|---|---|
| 3,860,486 | 1/1975 | Keyes et al. | 195/68 |
| 3,956,219 | 5/1976 | Smithwick, Jr. | 260/30.2 |
| 4,419,444 | 12/1983 | Quash | 435/174 |
| 4,475,236 | 10/1984 | Hoffman | 356/39 |
| 4,492,752 | 1/1985 | Hoffman et al. | 436/519 |
| 4,499,052 | 2/1985 | Fulwyler | 422/52 |
| 4,526,276 | 7/1985 | Shoor et al. | 209/552 |
| 4,542,104 | 9/1985 | Stryer et al. | 436/536 |
| 4,574,116 | 3/1986 | Kaplan et al. | 435/68 |
| 4,584,277 | 4/1986 | Ullman | 436/518 |
| 4,596,035 | 6/1986 | Gershman et al. | 356/340 |
| 4,665,020 | 5/1987 | Saunders | 436/523 |
| 4,717,655 | 1/1988 | Fulwyler | 436/534 |
| 4,762,701 | 8/1988 | Horan et al. | 514/824 |
| 4,775,619 | 10/1988 | Urdea | 435/6 |
| 4,783,401 | 11/1988 | Horan et al. | 435/34 |
| 4,786,165 | 11/1985 | Yamamoto et al. | 356/23 |
| 4,859,584 | 8/1989 | Horan et al. | 435/29 |
| 4,869,903 | 9/1989 | Lifson et al. | 514/8 |
| 4,918,004 | 4/1990 | Schwartz | 436/534 |
| 4,960,713 | 10/1990 | Hadfield et al. | 436/534 |
| 4,987,086 | 1/1991 | Brosnan et al. | 435/4 |
| 4,988,619 | 1/1991 | Pinkel | 435/30 |
| 5,073,497 | 12/1991 | Schwartz | 436/10 |

FOREIGN PATENT DOCUMENTS

| | | |
|---|---|---|
| 0145386 | 6/1985 | European Pat. Off. . |
| 2627286 | 8/1989 | France . |
| 1561042 | 2/1980 | United Kingdom . |
| US/92/05799 | 4/1992 | WIPO . |

OTHER PUBLICATIONS

McHugh, T. M., "Flow Cytometry and the Application of Microsphere-Based Fluorescence Immunoassays", *Immunochemica*, vol. 5 (1991).

Shapiro, H. M., *Practical Flow Cytometry*, Ch. 7, pp. 115–198 (1988).

Gosling, "A Decade of Development in Innunoassay Methodology", *Clin. Chem.*, vol. 36, pp. 1408–1427 (1990).

Sigma, *Immunochemicals Catalog*, p. 285 (1992).

*Cappel Product Guide* (1991).

Rylatt et al., "A Rapid Whole-blood Immunoassay System", *The Medical Journal of Australia*, vol. 152, pp. 75–77 (1990).

Brinchmann et al., "Direct Immunomagnetic Quantification of Lymphocyte Subsets in Blood", *Clin. exp. Immunol*, vol. 71, pp. 182–186 (1988).

Saunders et al., "Flow Cytometric Competitive Binding Assay for Determination of Actinomycin-D Concentrations", *Cytometry* vol. 11, pp. 311–313 (1990).

Bangs, "Latex Agglutination Tests", *Am. Clinical Lab. News Edition* (1988).

Cantarero et al., "The Adsorptive Characteristics of Proteins for Polystyrene and Their Significance in solid-Phase Immunoassays", *Analytical Biochemistry*, vol. 105, pp. 375–382 (1980).

Holodniy et al., "Detection & Quantification of Human Immunodeficiency Virus RNA in Patient Serum by Use of the Polymerase Chain Reaction", *J. Infectious Dis.*, vol. 163, pp. 862–866 (1991).

Montagne et al., "Polyacrylic Microspheres as a Solid Phase for Microparticle Enhanced Nephelometric Immunoassay (Nephelia (R)) of Transferrin", *J. of Immunoassay*, vol. 12, pp. 165–183 (1991).

Lisi et al., "A Fluorescence Immunoassay for Soluble Antigens Employing flow Cytometric Detection", *Clinica Chimica Acta.* vol. 120, pp. 171–179 (1982).

Saunders et al., "Amplified Flow–Cytometric Separation–Free Fluorescence Immunoassays", *Clin. Chem.*, vol. 31, pp. 2020–2023 (1985).

Wilson et al., "A New Microsphere-based Immunofluorescence Assay using Flow Cytometry", *J. Immuno. Meth.*, vol. 107, pp. 225–230 (1988).

(List continued on next page.)

Primary Examiner—David Saunders
Assistant Examiner—Christopher L. Chin
Attorney, Agent, or Firm—Bertram I. Rowland

[57] ABSTRACT

A method for detecting multiple subpopulations of analytes of interest in a sample employing a complementary binding moiety to each of said analytes bound to a solid support, wherein each analyte and its complementary binding moiety comprise first and second members of a specific binding pair (msbp) respectively is provided. The method includes the steps of forming a mixture of known proportions of multiple subpopulations of said complementary binding moieties, wherein each subpopulation comprises a different complementary binding moieties, contacting the sample with the mixture so that specific binding pairs are formed on the solid supports, and relating the presence of analytes of interest in the sample to the formation of specific binding pairs associated with each unique proportion of said multiple subpopulations. The method can be performed with solid supports of a single average size and a single fluorochrome and without the need for using three detection systems (fluorescence FS & SS). Also provided is a relatively low cost flow cytometer which can be used with the subject method.

5 Claims, 3 Drawing Sheets

OTHER PUBLICATIONS

Kronick et al., "Immunoassay Techniques with Fluorescent Phycobiliprotein Conjugates", *Clin. Chem.*, vol. 29, pp. 1582–1586 (1983).

Allain et al., "Automated Fluoroimunoassay of Theophylline and Valproic Acid by Flow–Injection Analysis with Use of HPLC Instruments", *Clin. Chem.*, vol. 35, pp. 469–470 (1989).

Goding, "Conjugation of Antibodies with Fluorochromes: Modifications to the Standard Methods", *J. of Immun. Methods*, vol. 13, pp. 215–226 (1976).

Cuatrecasas et al., "Selective Enzyme Purification by Affinity Chromatography", *Proc. Nat. Acad. Sci.*, vol. 61, pp. 636–643 (1968).

Hijmans et al., "An Immunofluorescence Procedure for the Detection of Intracellular Immunoglobulins", *Clin. exp. Immunol.*, vol. 4, pp. 457–472 (1969).

Bangs, "Microsphere–Based Tests and Immunoassays for Fun and Profit", Bangs Laboratories Seminar (1991).

Lindmo et al., "Immunometric Assay by Flow Cytometry using Mixtures of Two Particle Types of Different Affinity", *J. of Immunol. Methods*, vol. 126, pp. 183–189 (1990).

McHugh et al., "Detection of Human Erythrocyte Surface Antigen Gerbich . . . ", *Vox Sanguinis*, vol. 53, pp. 231–234 (1987).

Rhone–Poulenc, "Estapor–brand Microspheres", Bangs Laboratories Technical Reference #21.

Lee et al., "Thoughts on the Use of Immunoassay Techniques for Pesticide Residue Analysis", *J. Assoc. Off. Anal. Chem.*, vol. 74, p. 893 (1991).

Dixon–Holland et al., "Competitive Direct Enzyme–Linked Immunosorbent Screening Assay", *J. Assoc. Off. Anal. Chem.*, vol. 74, pp. 784–789 (1991).

Noah et al., "Efficiency of Two Commercial Elisa Kits Compared with the Bam Culture Method for Detecting Listeria in Nat. Contaminated Foods", *J. Assoc. Off. Anal. Chem.*, vol. 74, pp. 819–812 (1991).

Beaver et al., "Comparison of an Elisa–based Screening Test with Liquid Chromatography for the Determination of Aflatoxins in Corn", *J. Assoc. Off. Anal. Chem.*, vol. 74, pp. 827–829 (1991).

Scillian et al., "Early Detection of Antibodies Against rDNA–Produced HIV Proteins With a Flow Cytometric Assay", *Blood*, vol. 73, pp. 2041–2048 (1989).

Scouten (Ed), *Solid Phase Biochemistry, Analytical and Synthetic Aspects*, p. 779 (1983).

Walker et al., (Eds), *Techniques in Molecular Biology*, pp. 113–135 and 273–283 (1982).

Botchan et al., "The Arrangement of Simian Virus 40 Sequences in the DNA of Transformed Cells", *Cell*, vol. 9, pp. 269–287 (1976).

Jeffreys et al., "A Physical Map of the DNA Regions Flanking the Rabbit beta–Globin Gene", *Cell*, vol. 12 pp. 429–439 (1977).

Southern, "Detection of Specific Sequences Among DNA Fragments Separated by Gel Electrophoresis", *J. Mol. Biol.*, vol. 98, pp. 503–517 (1975).

Williams et al.(Eds), *Methods in Immunology and Immunochemistry*, vol. 1, pp. 120–187 (1967).

Maniatis et al., "The Identification of Recombinant Clones", *Molecular Cloning*, pp. 309–311 (1982).

Fulwyler et al., "Flow Microsphere Immunoassay for the Quantitative and Simultaneous Detection of Multiple Soluble Analytes", *Methods in Cell Biology*, vol. 33, pp. 613–619 (1990).

Bangs Laboratories Technical Reference #21, "Particles Used in DNA Probes".

METHOD AND COMPOSITION FOR THE SIMULTANEOUS AND DISCRETE ANALYSIS OF MULTIPLE ANALYTES

ACKNOWLEDGEMENTS

This invention was supported in part by grants from National Heart, Lung and Blood Institutes CONTRACT NO1-HB-6-7020. The U.S. Government may have rights in this invention.

This is a continuation of application Serial No. 07/731,039, filed Jul. 16, 1991, now abandoned.

INTRODUCTION

Technical Field

The present invention relates to a method and apparatus for use therein for the simultaneous detection of multiple analytes in a biological sample using multiple complementary binding moieties. The invention is exemplified by the simultaneous detection of human IgG and antibodies to HIV gp41, HIV p24 and Hepatitis B core protein.

BACKGROUND

The in vitro diagnostics industry has been seeking technologies which afford the simultaneous discrete detection of multiple analytes. As an example, chlamydia and gonorrhea infections often are coincident in women. Collecting a specimen can be problematic so that a single assay which can detect both disease agents simultaneously is desirable. Another example is the current interest in Europe in the simultaneous detection of HIV-1 and HIV-2 antibodies in blood. Using present technology, a positive finding indicates the presence of antibodies to either one or both of the viruses but does not allow a determination of which antibody, specifically, is present. Such an assay technology has somewhat less diagnostic utility than a discrete assay affords but offers a measure of convenience and cost effectiveness.

Another reason for the interest in the simultaneous, discrete analysis of multiple analytes lies in the use of such technology in so called panel testing and screening assays. In panel testing, for a given specimens under diagnostic interrogation a number of different assays are always ordered together for the purpose of diagnostic interpretation. In screening assays, the laboratory always performs the same set of assays on every specimen in an effort to determine if the specimen is positive for one or more of the analytes in the screen.

An example of the latter application is screening of blood in the blood bank where every unit of donated blood is screened for HIV, HBV, HTLV, and HCV. In either of these situations a reagent technology which afforded the simultaneous discrete analysis of multiple analytes in a single reagent would have obvious cost and convenience benefits. Presently this need for efficient screens or panels is accommodated using robotics where multiple but separate assays are performed by a preprogrammed reagent and sample handling system. Such systems are expensive and can be unreliable.

It is therefore of interest to develop the capability to allow the medical diagnostician to perform multiple discrete simultaneous analyses of several analytes. It is also of interest to develop a low cost apparatus for carrying out multiple simultaneous analyses.

Relevant Literature

Recent review articles trace the history of the technological evolution of concepts for multiple simultaneous immunoassays (Fulwyler and McHugh, Methods in Cell Biology 33:613–619,1990 and McHugh, Immunochemica 5: No. 1, 1991). These concepts trace back to UK patent #1561042 assigned to Coulter Inc. by Fulwyler in 1976. All of these methods involve the use of separately identifiable subpopulations of immunoreactive microspheres which can be detected in a flow cytometer. Related U.S. patents include U.S. Pat. Nos. 4,499,052, 4,526,276, 4,717,655. Detection of cells using a flow cytometer has also been disclosed in the following U.S. patents, U.S. Pat. No. 4,859,584, U.S. Pat No. 4,783,401 and U.S. Pat. No. 4,762,701.

Simultaneous determination of multiple immunoreactive analytes employs the use of fluorescent immunoassays (FIAs) in which the capture matrix or so called solid phase generally is a microsphere of known diameter. For example a 10 micron bead can be coated with an antigen (A). When this coated bead is exposed to a fluid with contains antibodies to antigen (A) these antibodies will specifically bind to the coated bead. Next a reagent which contains a fluorochrome labelled antibody which will specifically bind to antibody A is added. Thus an antibody "sandwich" arises when antibody (A) is present in the sample such that the fluorochrome is now bound to the bead via the specific antibody-antigen pairing. This is an example of an "antibody capture" FIA. Alternatively the bead can be coated with certain antibodies and thus selectively capture antigens which might be present in the sample in an "antigen capture" immunoassay. In this manner the effective fluorescence of the 10 micron bead is determined by how many specific antigens or antibodies are captured, i.e., are present in the sample.

Since the flow cytometer can co-determine particle size and fluorescence intensity, several different immunoassays can be simultaneously performed on the same sample by coating differing sizes of beads with different analytes, i.e., one immunoassay per bead size (see Fulwyler supra). All applications of this technology to the simultaneous discrete detection of multiple analytes rely upon the use of flow cytometry to discriminate one analyte from another based upon the differing sizes of the microspheres employed. Thus the number of different analytes which can be so differentiated is determined by the particle size resolution capabilities of FACS technology and upon the number of different sizes of microspheres which can be reliably manufactured to a precise size.

SUMMARY OF THE INVENTION

The subject invention provides for the performance of simultaneous assays to detect multiple analytes of interest in a sample using a mixture of multiple discrete populations of complementary binding moieties attached to a solid support which can be detected in a flow cytometer. The solid support to which each discrete population is attached may be of the same size for each population, or different sizes. Each analyte and its complementary binding moiety comprise first and second members of a specific binding pair (msbp), respectively. The method involves preparing a mixture of discrete subpopulations of solid supports to which each second msbp is bound so that the mixture contains a known proportion of each discrete subpopulation, contacting the mixture with the sample for a time and under conditions whereby specific binding pairs are formed on the solid supports, detecting a preselected number of supports and relating the presence of particular analytes of interest to the formation of specific binding pairs associated with each of the discrete populations. The specific binding pairs are detected by means of a detectable label.

The method of analysis of the data obtained includes the steps of collecting data by way of the detectable label for a predetermined number of solid supports as a function of the intensity of the label for each of the preselected proportions of complementary binding moieties. The relative intensity of the label can be used to indicate the presence or absence of an analyte of interest in the sample.

The apparatus of the subject invention is for detecting fluorescence from a sample containing solid supports flowing in a liquid path. The apparatus includes means for detecting at least one fluorochrome capable of excitation and means for accumulating the total number of particles and/or total fluorescence associated with each of the several subpopulations of solid supports. Means of recording the data collected is provided so that the relative intensity of fluorescence collected for a predetermined number of solid supports may be associated with each of the preselected ratios of binding moieties.

The methods of the subject invention greatly extend the number of simultaneous analyses that may be performed on a single sample and find particular application in screens, panels and combination tests of all types. The apparatus provides an alternative to traditional flow cytometers for particle analysis, and finds particular application with the method of the subject application.

BRIEF DESCRIPTION OF THE SPECIFIC EMBODIMENTS

In accordance with the subject invention compositions and methods and an apparatus are provided for the performance of simultaneous discrete assays of multiple analytes of interest in a sample, particularly a biological sample. The analytes may be polypeptides such as antigens, antibodies, nucleic acids, haptens, carbohydrates or combinations thereof. The method relies upon the use of a mixture of known proportions of complementary binding moieties to each analyte of interest; each analyte and its complementary binding moiety comprise first and second members of a specific binding pair (msbp), respectively. Each complementary binding moiety is attached to a solid support, generally a microsphere, that may be detected by flow cytometry techniques. The identification of the analyte does not depend upon the size or other physical characteristic of the solid support to which the complementary binding moiety is bound. Therefore, all complementary binding moieties may be bound to solid supports of the same average size, although more than one size may be used if desired or if the number of analytes to be detected is particularly large.

The subject invention allows the performance of simultaneous discrete analysis of multiple analytes without reliance upon bead size discrimination. Further, it allows the simultaneous performance of a larger number of assays than can be accomplished with the conventional use of FACS and immunoreactive beads as described heretofore. At least four, generally five or six analytes may be assayed simultaneously using a single bead size-and/or a single fluorochrome. Adding multiple bead sizes or other physical discriminators or the use of additional fluorochromes may be used to increase the number of analytes assayed simultaneously.

Figure 2:
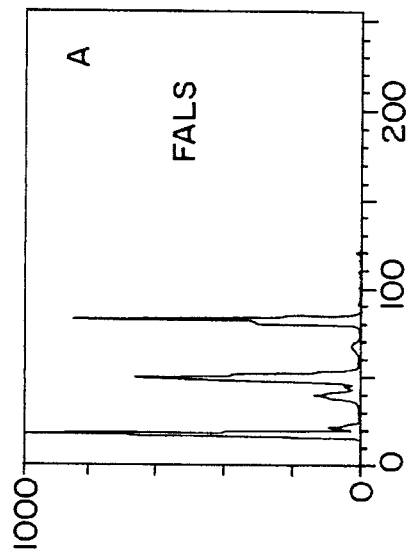
FIG. 2 is a graphic representation of a single parameter forward light scatter histogram of the three bead populations represented in FIG. 1.

In a conventional assay, the results of the performance of immunoassays on microspheres in FACS or "flow" instrumentation are interpreted in the following way: When right angle light scattering of incident light is plotted against forward angle light scattering of incident light, the resultant is a series of derivative functions of microsphere size as shown below in FIG. 1. Each of the profiles in this two parameter light scatter profile defines a bead population of a particular size. Alternatively, in a single parameter profile in which only forward angle light scattering (FALS) is plotted, the number of events, i.e., the number of beads of that size which passed through the light path, can be plotted as shown in FIG. 2. Computer aided reduction of these data is used to "gate" the data such that only the data from beads of a particular size is viewed, i.e., only the number of events at certain FALS values are shown. By "gate" is intended that only a population(s) of beads of a size within a specific size range are considered in analysis of the data. McHugh (supra) has demonstrated that adequate separation of bead populations can be achieved using FALS only.

Figure 3A:
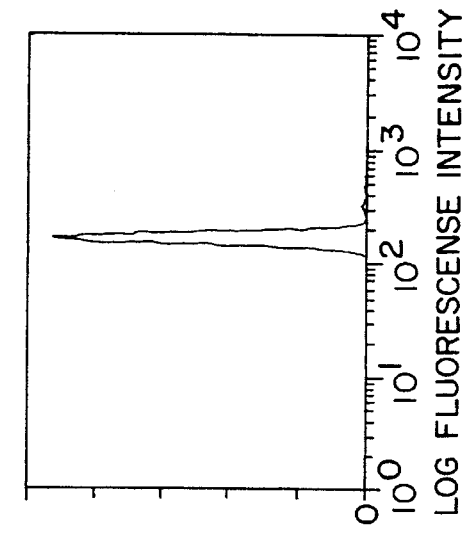
FIG. 3(A–B) are a graphic representation of fluorescence histograms of microspheres stained with FITC anti-human IgG.
Figure 3B:
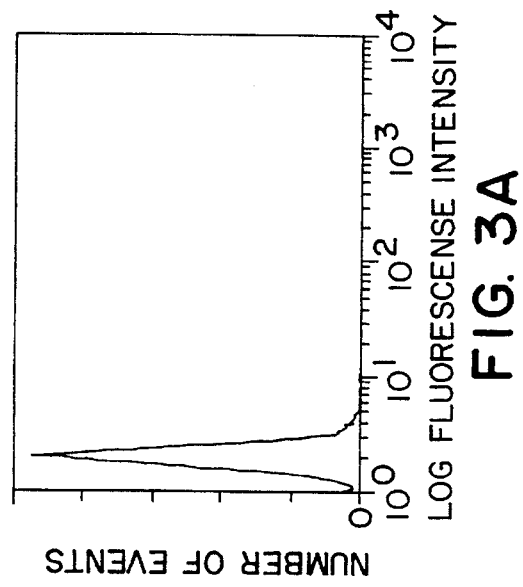

When analyzing the data from FIAs done on beads of varying sizes the gating technique above is used to focus upon one bead size population at a time. Within this "gate" the fluorescence intensity of the beads of that size is determined by the degree of binding of the analyte in the immunosandwich. These data are output in the form of a histogram as shown in FIG. 3. Here the number of events, i.e., the number of beads of that size which passed through the light path, is plotted against the fluorescence intensity of those beads on a log scale.

Figure 1:
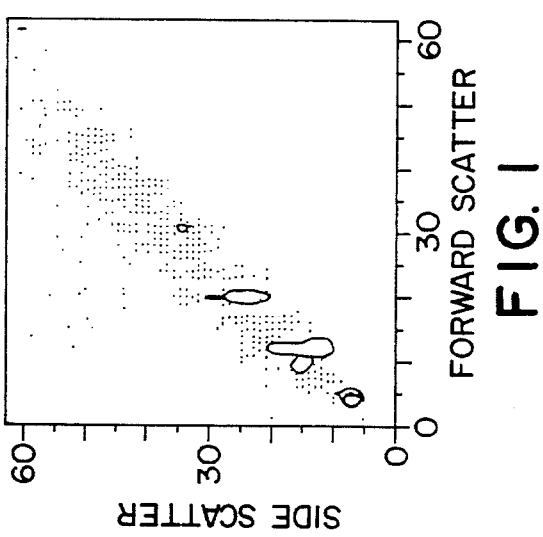
FIG. 1 is a graphic representation of a two parameter contour plot or gate showing the union of side scatter and forward scatter of three different size microsphere populations.

If the sample were a serum sample, for example, a positive serum would reveal a "peak" relatively further towards the right on the X axis than would a negative serum. However even a negative serum will have a representative peak because of nonspecific binding of the fluorochrome labelled second antibody to the bead. The position of the peak on the log scale X axis i(fluorescence intensity) is reported as the "mean channel fluorescence(mcf)". Thus the mcf value of a histogram peak is a measure of the degree of reactivity, i.e., presence of the analyte, wherein the analyte is specifically identified by the "gate" in which the histogram lies. Of course this gate is determined by the bead size as shown in FIGS. 1 and 2. The area under the histogram peak has not previously been used to convey analytical information.

Using this methodology, wherein each analyte is detected via an immunoassay performed on a preselected and unique size bead and wherein each bead size determines the electronic gate within which fluorescence intensity can be determined, simultaneous discrete immunoassays for multiple analytes have been performed since 1974. This methodology is limited by the number of gates which can be resolved and the numbers and kinds of microspheres which are available. Scillian et ail (BLOOD 73:2041–2048, 1989) reports; four simultaneous antibody capture assays.

Two issues are noteworthy. One is the standard methods by which investigators in this field configured these multiple bead reagents and the other is the way in which the gated histogram data is reported. For the gated histogram data (see FIG. 3) the Y-axis is often labelled "RELATIVE number of events". The actual enumeration of the Y-axis values could be expressed as ABSOLUTE numbers of events. Further, it is standard practice to mix the multiplex reagents such that the number of beads of each size is the same as for all other sizes in the common reagent i.e. they are mixed in equal proportions or even if they are mixed in different proportions, significance is not realized. This practice also leads to an internal consistency in the size and shape of the peaks in the histogram which can mask certain properties of this technology.

In the subject method, it is possible to screen simultaneously for multiple analytes, without relying upon the physical characteristics of the beads or on using multiple flurochromes. Identification of the presence or absence of an analyte in the sample instead may be made by mixing a known proportion of each subpopulation of complementary binding moieties to form a reagent composition. The composition will comprise multiple discrete sub-populations of complementary binding moieties linked to particulate supports capable of detection by flow cytometry techniques. The proportion that each sub-populations constitutes of the total composition is later used in identifying an analyte of interest. Once the composition has been prepared, it is then combined with a sample using appropriate buffers, temperatures, and time periods so that specific binding pairs may form. Unbound reagents are removed and the specific binding pairs contacted with a labeling agent. Unbound labeling agent is removed and a predetermined number of solid supports are then detected using flow cytometry techniques. The relative intensity of label agent associated with the solid supports is collected and the data plotted as a histogram of number of events versus relative label intensity. The data are then analyzed to identify analytes present in the sample based upon the proportion of each subpopulation of reagents used in the essay.

In some instances, it may be advantageous to use properties so,that any combination of two or more subpopulations of binding moieties is also unique. For example, if there are three analytes of interest, three unique nonadditive proportions of complementary binding moieties could be 1:2:7. If a specified number of solid supports is then counted, for example 5000, then the number of solid supports associated with each subpopulation, based upon the proportion present in the original reagent, would be 500, 1000, and 3500. If all three analytes were absent from the sample, then a population of 5000 solid supports would be identified having background fluorescence. If two of the analytes were present in the sample which are bound by the binding moieties which were present at 10% and 20% of the original reagent composition, then two populations could be identified, one representing the 70% subpopulation for which no analyte is present and together one representing the remaining two subpopulations which represent 30% of the mixture. Where the two analytes are present in differing amounts, then three separately identifiable subpopulations would be observed based upon the relative intensity of label detected. This is illustrated further below. The assay method of the invention can be used to detect any analyte that is capable of binding to a complementary binding moiety. Generally, the analyte will be a polypeptide, protein, carbohydrate polysaccharide, nucleic acid, drug of abuse or a metabolite of such a drug or combinations thereof.

For the most part, the analytes detected or quantified in accordance with the present invention will preferably have a molecular weight of at least about 5,000, more usually at least about 10,000. Polypeptides of interest will generally be from about 5,000 to about 5,000,000 molecular weight, more usually from about 10,000 to 1,000,000 molecular weight. Where the analyte is a nucleic acid molecule, the molecule will generally range from about 12 nucleotides to about $2\times10^6$ nucleotides. The nucleic acid sample can involve DNA, which can be chromosomal or extrachromosomal, e.g., plasmids, viruses, synthetic constructs, or the like, or RNA, such as messenger RNA transfer RNA, ribosomal RNA, viruses, or the like. The nucleic acid sequences can involve structural genes on translated regions, regulatory regions, introns, exons, and the like. Analytes for detection or quantitative with the present invention can also have molecular weight of less than about 5,000. Examples of suitable analytes with a molecular weight of less than 5,000 include small polynucleotides, small polypeptide hormones, steroid hormones, cholesterol, drugs, drugs of abuse and toxins. The complementary binding moieties are components capable of specific binding to the particular analyte of interest. The binding between the binding moieties and the analyte of interest is preferably noncovalent. Suitable binding moieties preferably have higher affinity and specificity for the analyte than for the other components in a sample for analysis. Suitable binding moieties can be of a variety of molecular categories including antibodies, in particular, and preferably, monoclonal antibodies specific for a portion of the analyte; binding proteins that naturally bind to the analyte, e.g. lectins for analytes comprising a carbohydrate portion; and ligand receptors when the analyte comprises a complementary ligand. Some examples of binding moieties include: anti-HBsAg antibody either animal derived polyclonals or mouse monoclonals; HIV gp 41 purified from the virus or derived by recombinant DNA technology; concanavalin A; jaclin; and CD4 from human T lymphocytes.

When the analyte is a nucleic acid, the binding moiety can be ssDNA, RNA, or any other natural or synthesized single stranded nucleic acid. Alternatively the binding moiety could be a nonnucleic acid molecule which recognizes a specific nucleotide sequence, such as an antibody or specific DNA binding protein on the analyte.

Methods for the production of antibodies or monoclonal antibodies to be used in the subject invention are known in the literature. See, e.g., U.S. Pat. No. 4,574,116 and the references cited therein, whose disclosures are herein incorporated by reference. Alternatively, monoclonal antibodies or binding fragments can be purchased commercially.

When the binding moiety is a nucleic acid molecule, the moiety will usually comprise at least 8 nucleotides, more usually 10 nucleotides, and preferably at least about 12 nucleotides. The size of the binding moiety will vary with the nature of the analyte, the amount of analyte in the sample, and the conditions employed in the detection process. The nucleic acid sequences for use in a binding moiety can be provided by isolation from a natural source, synthesis, or other means known in the art.

The sample can be subjected to prior preparation or can be used without prior treatment. The protocol for the assay can accommodate the simultaneous detection of both antibodies and antigens. One subpopulation of beads is coated with antigen and another population is coated with antibodies derived from an animal species such as goat, mouse, rat, rabbit, etc. The second reagent contains fluorescent labelled antibodies of at least two types. In the case where the sample is of human origin the second reagent includes anti-human antibodies which will selectively bind with any analyte antibody which has bound to the antigen coated bead above and, for example, goat antibody which will selectively bind the analyte antigen in the sample which has bound to the antibody coated bead. The two antibodies in the second reagent will not cross react because they are idiotypically distinct. These labelled antibodies do not need to be in any particular proportion in the reagent so long as both are present in excess.

In the situation in which the analyte in the sample is capable of binding with the binding moieties, no prior sample preparation is generally necessary. In the situation in which the analyte in the sample is not immediately capable of binding with the binding moieties, prior sample preparation will be necessary. For example, where the analyte is double stranded nucleic acid and the binding moieties are complementary nucleic acid strands, it will be necessary to treat the sample to denature the double-stranded molecules before mixing with the binding moiety. Denaturation can be achieved most readily by subjecting the sample to high temperature, generally from about 90° C. to about 100° C. for about 3 to about 15 minutes. Other means for denaturation can be used such as treating the sample with alkaline solutions or concentrated solutions of formamide or through use of other procedures known in the art.

The solid supports preferably will comprise particles of beads having an average diameter of about 0.25 μ to about 100 μ, most preferably about 2 μ to about 15 μ where cost may be a factor (small beads are less expensive than large beads). The size of the beads is not critical to the practice of the subject invention. Suitable materials for the solid supports include organic polymers, both naturally occurring and synthetic, such as polysaccharides, styrene polymers, polyacrylates, e.g., polyacrylamide, hydroxyethyl polymethacrylates, glass, ceramic, carbon, polyvinyl chloride, protein, and the like. Styrene polymers include polystyrene, polymers containing aromatic moieties, and higher aromatic compounds such as naphthalene, anthracene, etc. The solid supports preferably consist of a latex compound.

Bifunctional organic linking groups can be used to attach the complementary binding moiety to the solid support. Examples of such groups, which are well known in protein chemistry, include dialdehydes, such as glutaraldehyde, and diamines, such as 1,6-diaminohexane, Such bifunctional organic linking groups are preferably used when the binding moiety is sufficiently large to prevent complementation.

The various solid supports can be functionalized or non-functionalized, preferably functionalized for covalent bonding to the binding moiety. When the linking element is a polymeric material, various procedures are known in the art for the activation of polymer surfaces and the attachment of immunoglobulins, glycoproteins, saccharide-containing organic molecules, and polynucleotides. See U.S. Pat. Nos. 4,419,444; 4,775,619; 3,956,219; and 3,860,486 as well as European Patent Application No. 84308143.1 and Scouten, W. H. (ed.) *Solid Phase Biochemistry, Analytical and Synthetic Aspects* (1983), Wiley & Sons, New York, page 779.

The protocol for the assay can be varied widely, depending upon the system being employed, the sensitivity of the assay, the speed with which the assay is to be carried out, the nature of the analyte, and the like. The binding moiety and sample are combined together under appropriate conditions to allow for binding. The reagents can be combined concomitantly or added sequentially. Where the order is sequential the reaction mixture of the sample, the binding moiety and buffer is preferably incubated for about 5 to 90 minutes, usually about 30 minutes, before washing the mixture and the addition of labelled reagent. A fluorochrome label is generally and preferably used for such a purpose by providing a detectable label upon excitation of the fluorochrome with energy of the appropriate wavelength. The amount of analyte in the sample can then be determined by comparing the amount of detectable label to that formed in the presence of a known amount of analyte.

The fluorochrome typically and preferably employed results in a change in the amount of light absorbance (optical density) or emission of the assay medium when excited by energy of the appropriate wavelength. Preferred fluorochromes include fluorescein isocyanate, phycoerythrin, Duochrome, allophycocyanin, PE Tandem, ultralite 700 and Texas red and are commercially available. The fluorochromes are generally used at F to P molar ratio of about 1 to about 5. Other fluorochromes are used in concentrations to provide comparable signals to FITC.

The present invention contemplates the use of light emitting moieties other than fluorochromes such as phosphorescent, chemiluminescent or bioluminescent moieties. When these light emitting labels are used as dyes, a laser is not required so that the derivative apparatus employs a fluidics device and a light detector with the appropriate electronics.

The sample is combined with the mixture containing the known proportion of immunobilized complementary binding moieties and incubated for a time sufficient for specific binding pairs to form.

The amount of sample that can be used in conjunction with the present invention depends, among other things, upon the concentration of the analyte, the nature of ithe sample, and the sensitivity of the assay. Incubation time is dependent on a number of factors including temperature, pH, ionic strength, etc. In general binding of polypeptides can require as little as 5 minutes at 37 degrees C. up to 24 hours at 4 degrees C. Similarly nucleic acid hybridization is dependent oin the same physical conditions as well as being dependent on GC content of the nucleic acid. In general hybridization requires as little as 2 hours at 42 degrees C. up to 48 hours at 42 degrees C. Following incubation, the labelled reagent is added and the incubation continued for 5 to 90 minutes. Preferably, standard solutions are prepared of known concentrations of analyte to serve as standards for comparison with the sample. In this way, accurate quantitative determinations can be obtained.

The assay medium is preferably buffered at a pH in the range of about 6 to 9, with a convenient buffer such as phosphate, tris, or the like. The significant factor in selecting an appropriate buffer is that the buffer not inhibit the binding of the specific binding pairs.

The assay can be carried out at any suitable temperature which does not inhibit the desired reactions, generally about 20° C., but preferably at an elevated temperature below about 40° C. The assays are generally and preferably performed at atmospheric pressure.

The time required for the completion of the desired reactions may vary depending on the particulars of the assays. In a situation, for example, in which the binding moiety is a nucleic acid, the time required for hybridization or binding depends on the concentration and sequence complexity of the nucleic acid probe, as well as on the assay temperature, solvent, and salt concentrations. Generally, hybridization is carried out at a temperature of about 20° C. to about 50° C. in about 0.15 M sodium chloride and 0.015 M sodium citrate for a period of about ½ hr. to about 18 hr. to allow formation of hybrids.

The techniques for the hybridization of DNA are disclosed in many references, including Walker and Gaastra (eds.) *Techniques in Molecular Biology* (1983) MacMillan Publishing Company, New York, pp 113–135 and 273–283; Maniatis et al., (eds) *Molecular Cloning* (1982) Cold Spring Harbor Laboratory, pp 309; E. Southern, *J. Mol. Biol.* (1875) 98:503; Botchan et al., *Cell* (1976) 9:269; Jeffreys et al., *Cell* (1977) 12:429. These disclosures are incorporated herein by reference.

Figure 4:
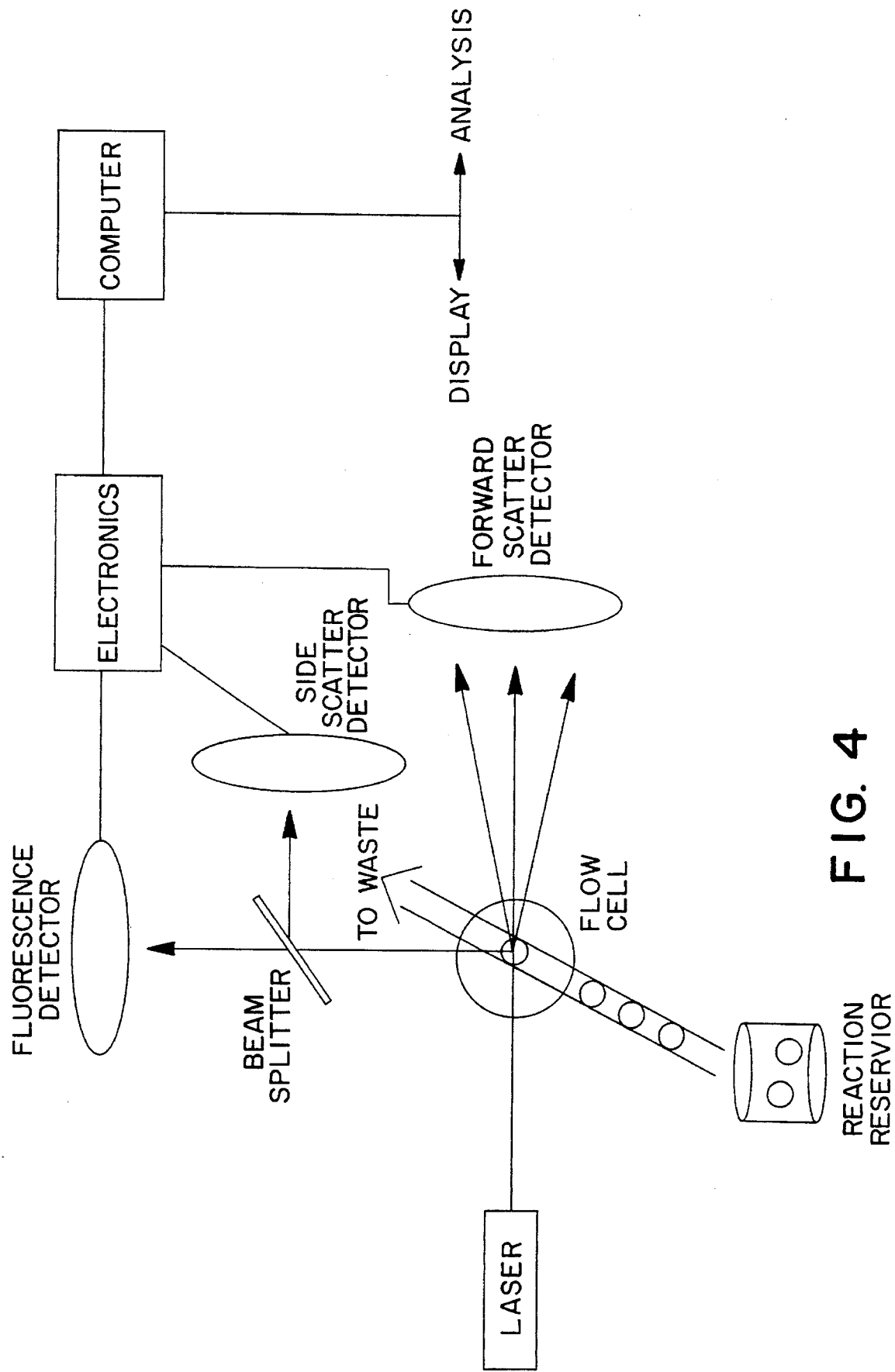
FIG. 4 is a schematic representation of a cytometric apparatus for detecting all of side scatter, forward scatter, and fluorescence, or two or more of these characteristics, in a combination, of individual reacted particles moving in a flow path from the reaction vessel.

In using the present invention, flow cytometry is the preferred method to detect the formation of, and optionally quantify, analyte-complementary binding moiety complexes and relate the information to the detection and determination of the amount of an analyte of interest present in the sample. The analysis of immunoreactive beads bound with a fluorescent dye in a flow cytometer has been described using a flow cytometer of conventional design as represented in FIG. 4 (See UK patent #1561042).

Existing methods of performing simultaneous analysis of multiple analytes rely upon the capability of a flow cytometer to simultaneously record side scatter and/or forward scatter of reflected light and light emitted from fluorochrome labelled microspheres. The intensity of forward scatter and side scatter of reflected laser light is determined by the size of the particle in the light path. The intensity of fluorescent light emitted at right angles to the light path is a function of the quantity of fluorochrome on the microsphere. The flow cytometer incorporates fluidics which permit only one microsphere at a time to cross the light path. Thus the size of the particle and its coincident fluorescence are co-determined.

In the convention of flow cytometers, flow microsphere-based immunoassays (FMIA) are performed in an appropriately configured reaction vessel. The reacted beads are passed through a flow cell which causes the microspheres to pass through a laser beam one at a time. The forward scattered light and side scattered light are gathered onto two detectors. The intensity of forward and side scattered light which is determined by the size of the particle in the beam is recorded with the appropriate electronics and stored in a computer for further analysis. The laser also excites the fluorescent dye specifically bound to the microsphere. The emitted light is collated to one of up to three fluorescence detectors. The intensity of the fluorescence is recorded with the appropriate electronics and stored for future analysis.

In this manner both the size and fluorescence of the microspheres are recorded. Since the intensity of fluorescence is determined by the number of fluorescent dye molecules associated with the bead, a solid phase immunoassay can be performed on the beads and analyzed in the flow cytometer (Fulwyler and McHugh, Methods in Cell Biology, Academic Press 33, 1990). Forward scatter and side scatter or forward scatter alone has been employed to discriminate bead sizes. Forward scatter alone has been shown to discriminate particles that differ by less than 1 micron (McHugh in Immunochemica Vol 5, 1991). Previously all FMIA have been performed using fluorescence detection in conjunction either with both forward scatter and side scatter or with forward scatter alone.

Figure 5:
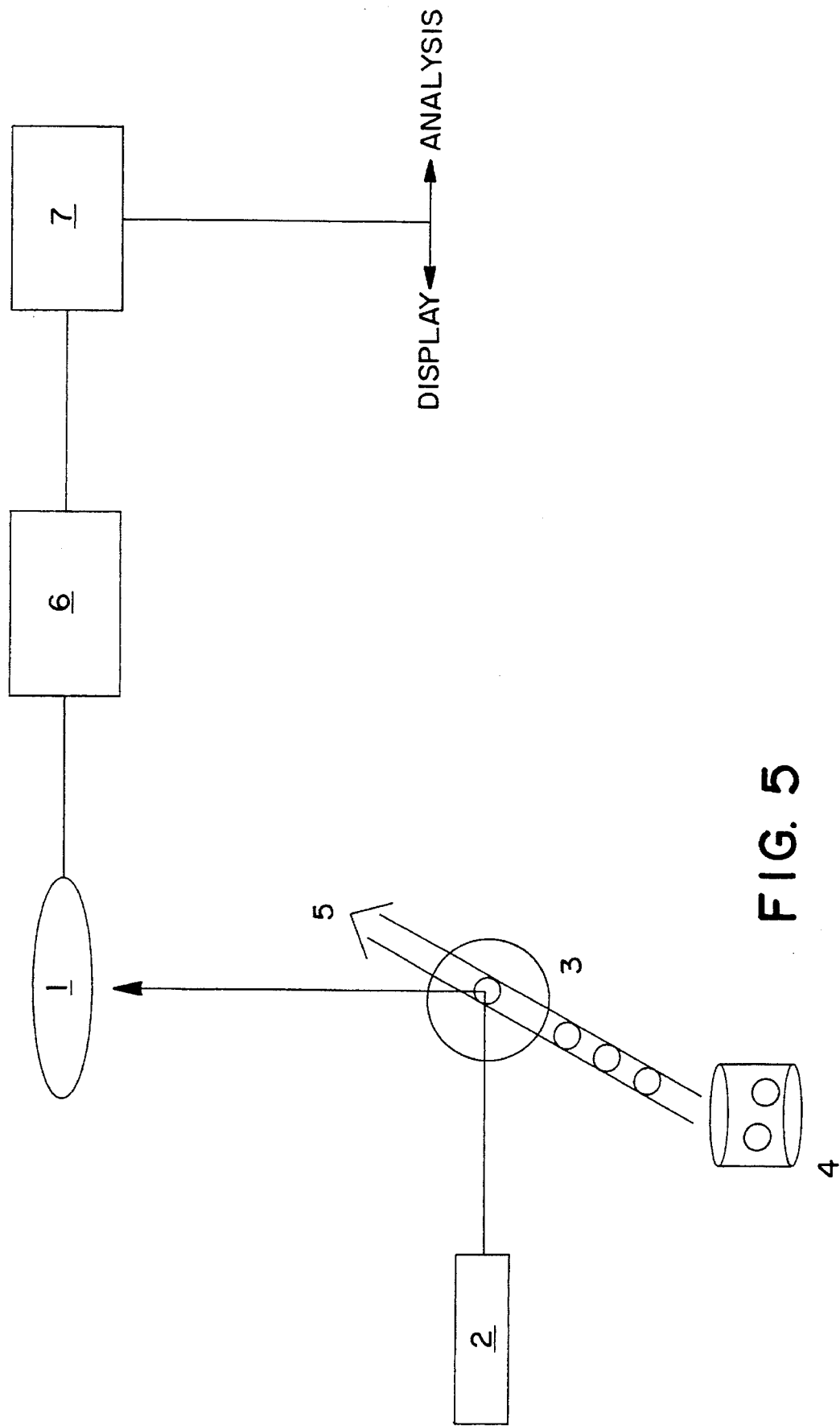
FIG. 5 is a schematic representation of a flow apparatus for detecting and analyzing fluorescence of individual reacted particles moving in a flow path from the reaction vessel.

In using the present invention a flow cytometer of a specific design as illustrated in FIG. 5 can be used instead of a traditional flow cytometer since there is no need to discriminate based upon bead size. So long as no size discrimination is needed, only fluorescence need be measured. In using the present invention, to perform analysis wherein it is necessary to discriminate bead size populations the apparatus shown in FIG. 5 is modified to include a side scatter detector and the appropriate electronics as illustrated in FIG. 4. With reference to FIG. 5, the flow cytometer is as follows: FMIAs (or any other specific binding assay such as a DNA Probe-nucleic acid assay) are performed in a suitable reaction vessel (4), reacted microspheres (8) are passed through a flow cell (3) and discarded to a waste vessel (5), and a laser (2) is employed to excite the chromophore used in the assay.

The reaction vessel can be a test tube, a well of a microtiter plate or other container. The laser can be any of an Argon laser, a HeNe laser, a diode laser, a UV laser, an Arc laser, a krypton laser or any other light source which emits a light of wavelength suitable to excite the particular dye employed in the assay. The fluorescence emitted by the excited chromosphere is collated onto one or more fluorescence detectors (1). The occurrence of a fluorescent event of intensity at or above a preselected intensity is recorded in the appropriate electronics (6) for analysis as is the quantitiation of that intensity. Data analysis is performed in a computer (7) using software of useful logic, or is performed manually.

As an internal control, included in the reagent mix can be a subpopulation of microspheres coated with the first of a binding pair wherein the second member of the binding pair is ubiquitous in samples to be analyzed by this method. Thus the absence of a positive resultant indicates that the method was employed erroneously, thus serving as a control on the reproducibility of the method when, for example large numbers of samples are analyzed manually or by an automated method. Examples of such ubiquitous analytes include but are not limited to immunoglobulins, highly conserved genomes, glycoproteinaceous enzymes, glycogen, components of cell membranes and the like.

Where multiple subpopulations of binding moieties are combined in an appropriate assay medium with the addition of a control sample (no analytes are present) and labelled reagent, where the label is a fluorochrome, following excitation of the sample, a background measurement of fluorescent activity may be obtained. For the most part, a low level of fluorescence will be obtained due to non-specific binding of the labelled reagent to the solid supports. This background fluorescence is not only acceptable, but is preferable in that it provides a means for identifying the subpopulation analytes which are absent from the sample. However, an essential requirement of this background activity is that it be distinguishable from activity which results from the presence of an analyte of interest in the sample.

The present invention contemplates assays in which the intensity of fluorescence decreases with the presence of analyte in the sample as is the case with competitive immunoassays, or fluorescence quenching assays of all types. In these cases both the histogram peak area and the mean channel fluorescence of the peaks associated with negative samples are predetermined by the reagent composition so that the amount of analyte can be calculated, i.e., the decrease in mean channel fluorescence of a peak of predetermined area is a direct measure of the amount of analyte in the sample associated with that peak area.

The present invention uses computer software to analyze data. The software 'logic' interrogates histograms of number of events versus fluorescence intensity to determine the best fit of the data with all possible predetermined combinations. The software also traces the pattern of the peaks found in the histogram and identifies the peaks, valleys and shoulders so that the areas (i.e., number of events) of fluorescence intensity ×1 through ×2, of each peak or combination of peaks can be calculated. Alternatively the data can be analyzed manually using printed histograms, such as those generated by commercially available flow cytometers and particle counters.

The present invention also contemplates a kit containing reagents for carrying out the present inventive method. The kit comprises, in separate containers or premixed, multiple subpopulations of complementary binding moieties to each of multiple analytes of interest generally each bound to populations of solid supports, wherein each analyte and its complementary binding moiety comprise first and second members of a specific binding pair (msbp). When bound to a solid support, the binding moieties may be provided in individual preselected proportions or as a mixture of preselected proportions. The kit may additionally include a separate container of a reagent labelled with a detectable label, particularly a fluorochrome which emits detectable fluorescence upon exposure to excitation energy, wherein said reagent is capable of binding to said first or said second msbp and allows for the detection of formation of any specific binding pairs.

Where the binding moieties are provided unattached to a solid support, the kit may additionally include solid supports and optionally reagents for attaching the binding moieties to the solid supports. Upon attachment of particular binding moieties to the solid supports of the kit, a mixture of the binding moieties can be formed in preselected unique proportions and the desired analyte of interest can be assayed.

EXAMPLES

Experimental Procedures

Materials:

Standard laboratory chemicals, purchased from various vendors including Sigma Chemical Co., Mallinckrodt, Inc., Fisher, Inc., etc., are used to make buffers.

Polystyrene microspheres of uniform diameters ranging from 2 to 10 microns can be purchased from several different vendors, including Polysciences, Inc., Seradyn, Inc. Bangs Laboratories, Inc., Flow Cytometry Standards Corp., and Duke Scientific, Inc.

Purified proteins, including conventional antigens as well as antibodies, to be coated onto the polystyrene microspheres may be derived from a variety of sources such as recombination DNA, tissue homogenates, viral, bacterial or cell lysates, and body fluids such as urine, plasma, ascites, etc. In many instances they can be purchased directly from vendors ("LinScott's Directory of Immunological and Biological Reagents", Sixth Edition, William D. Linscott, 1990–1991). If they are not readily available, they can be purified in the laboratory using conventional techniques.

Fluorescein isothiocyanate (FITC) labelled affinity purified anti-IgG IgG antibodies can be purchased from several vendors, including Caltag, Inc., Cappel, Inc., and Tago, Inc. Antibody purification and covalent coupling of FITC to purified IgG can also be accomplished in the laboratory using conventional techniques ("Methods in immunology and Immunochemistry", Eds., Curtis A. Williams and Merrill W. Chase, Volume 1, pp. 120–187, 1967, Academic Press, N.Y.).

Polystyrene and polyethylene test tubes can be purchased from several vendors, including Baxter, Inc. VWR, Inc., and Fisher, Inc. Microtiter plates with or without filters, as well as vacuum filtration manifolds can be purchased from Millipore, Inc. and Pall Biomedical Corp.

Reagent Preparation:

Preparation of the immunoreactive reagent involves two steps: (1) manufacturing immunoreactive beads (IRB) by coating polystyrene microspheres of a particular size with a protein antigen (Fulwyler and McHugh, In, "Methods in Cell Biology", Eds., H. A. Crissman and Z. Darzyneckiewicz, Vol. 33, pp. 613–619, 1990), and (2) mixing different preparations of IRB in predetermined proportions accurately.

(1) IRB Manufacture: A suspension of polystyrene microspheres is withdrawn out of the stock bottle, resuspended into fifty fold excess volume of deionized water ($dH_2O$), washed by filtration and counted either by direct visualization in a microscope or electronically using a semi-automated particle counter. The beads are then resuspended in an appropriate buffer (e.g., 50 mM sodium borate, pH 9.5) and incubated with an appropriate concentration ratio of protein to beads. The incubation time and temperature as well as the concentration ratio of beads to protein are determined empirically. The beads are then separated from unreacted protein by filtration, washed and resuspended in a storage buffer.

For example, IRB are employed for the detection of anti-HIV gp41 IgG antibodies in human sera. They are manufactured as follows: 4 micron beads (from Polysciences, Inc.) are washed as above and incubated with purified recombinant DNA-derived gp41 (from DuPont, Inc.) in 50 mM sodium borate buffer, pH 9.5, at a concentration of 4 µg gp41/107 beads/ml for 18 hours at 4° C. After washing and separation of unreacted gp41, the 4u-gp41 beads are stored at a concentration of $2 \times 10^7$ beads/ml at 4° C.

(2) preparation of a proportional reagent: An aliquot of each bead type specific for a particular analyte is withdrawn from the stock bottle and a substock is prepared in a large volume. The concentration of the various IRBs in the substocks are then determined by using an electronic particle counter. An appropriate volume based on the desired proportions of the IRB in the final reagent is then withdrawn from the substock and mixed together with other IRBs similarly aliquoted.

IRB Assay:

The assay for detection of analytes in serum or any other medium follows a two-step protocol as described below.

(1) Incubation of IRB with the medium to be screened: Sera or any other medium potentially containing the analytes of interest are mixed with IRB in an appropriate reaction buffer (e.g. PBS) at room temperature for 15 to 60 minutes. This may be carried out either in polypropylene test tubes or 96-well microtiter plates with or without filters. Following the incubation period the beads are washed repeatedly in order to separate unreacted analytes and minimize the binding of nonspecific components from the medium. The washing of beads can be accomplished either by centrifugation or by vacuum filtration if microtiter plates with filters are used.

(2) Reaction with FITC-labelled Protein: If the analytes of interest are IgG antibodies in human serum, the beads from above are resuspended in buffer containing FITC-labelled anti-human IgG. If the analytes are other proteins in human serum or any other medium the FITC label used is a conjugate of FITC coupled to an IgG antibody that specifically reacts with the protein analyte. The beads are then incubated at room temperature for an additional 15 to 60 minutes, washed and resuspended in buffer for analysis in a flow cytometer of the type described in FIG. 4.

DATA ANALYSIS

Data analysis is performed in the following way using a flow cytometer such as the Becton Dickinson FACScan:

1. Sample is introduced into the flow cytometer and an appropriate number of events (i.e. particles above the selected threshold value) counted, for example 4000 event counted. The events can be triggered by forward scatter, side scatter, or florescence above the appropriate threshold level. For example, a forward scatter threshold may be set at 348 to eliminate particles less than 2 microns in size, if desired.

2. The computer collects data on each particle for each of the preselected parameters such as FSC, SSC, FL1, etc.

3. The data is configured to output in the form of a florescence histogram where the Y-axis reports the number of events corresponding to each florescent channel shown on the X-axis. Depending on the design of the experiment one or more peaks will appear in the histogram.

4. Appropriate markers are set at fluorescent channel values to separate and calculate the area of each peak. The area of each peak as well as its mean channel flourescent (MCF) is diagnostic of the sample being examined.

EXAMPLE 1.

STRICT CORRELATION OF REAGENT

PROPORTIONS AND HISTOGRAM PEAK AREA.

A reagent was prepared using 4 micron diameter microspheres wherein the beads were coated with either recombinant HiV antigen gp41 or affinity purified goat antihuman IgG. Reagents containing exclusively either or both of these coated beads were blended proportionately so that beads coated with gp41 antigen comprised (within procedural error) 100%, 89%, 79%, 68%, 58%, 48%, 38%, 28%, 19%, 9% and 0% of the number of total beads in the reagent and beads coated with IgG comprised (within procedural error) 0%, 11%, 21%, 32%, 42%, 52% 62%, 72%, 81%, 91% and 100% respectively. Each of these 11 proportional reagents were contacted with human serum known to be positive for both IgG and gp41 antibodies by Elisa techniques and incubated for 40 minutes at room temperature. After washing a second reagent containing fluorescein(FITC) conjugated antihuman IgG antibodies (0.0076 mg/ml molar ratio F:P 5) was added to the reaction vessel and incubated for 20 minutes at room temperature. After washing the quantity of FITC associated with the reacted beads was analyzed by delivering the reaction mixture into a Becton Dickinson FACScan flow cytometer of a type as illustrated in FIG. 4 wherein 4000 events were accumulated by triggering on forward scatter and the fluorescence intensity of each event was recorded in computer memory.

These data were analyzed and output as a histogram of number of events (Y axis) versus log of fluorescence intensity (X-axis). 4000 total events were acquired via forward scatter triggering. Under these conditions one or two histogram peaks were observed depending upon whether the reagent contained one or two types of beads respectively. These peaks were observed as expected for a serum positive for both IgG and gp41, i.e., two nonoverlapping peaks. The areas of the peaks were calculated manually by placing a marker between the peaks and noting the number of events on either side of the marker. The peaks were observed to have different areas and the mean channel fluorescence of the peaks was consistent. The magnitudes of the peak areas thus measured varied in a manner predicted by the proportionality of beads in the reagents within experimental error as follows wherein the peak area was expressed as number of events within the peak as a percentage of the total number of events acquired: peak A contained 100.0%, 78.4%, 76.9%, 62.1%, 49.3%, 39.3%, 31.5%, 25.7%, 19.7%, 11.0% and 0.8% respectively of the total events acquired which percentages correlate with the reagent bead percentages first listed above for gp41 coated beads with a coefficient of correlation of 99.2% and peak B contained 0%, 17.0%, 28.0%, 33.7%, 45.6%, 50.8%, 60.6%, 66.5%, 72.5%, 81.6%, and 90.5% respectively which percentages correlate with the reagent bead percentages secondly listed above for IgG coated beads with a coefficient of correlation of 99.8%. Variance can be accounted for by error in the counting, measuring and mixing of coated bead reagents.

EXAMPLE 2

HISTOGRAM AREA IS INDEPENDENT OF FLUORESCENCE INTENSITY.

Using the methods described above it has been observed that the fluorescence intensity of a positive peak in a histogram can vary from one positive serum to another. The fluorescence intensity is reputed to be a function of the antibody titer. A serum known to be positive for HIV gp41 antibody was serially diluted 1×, 2×, 4×, 8× and 64× with a known negative serum. These panels Of diluted serum were separately contacted with one of four reagents containing, respectively, 80.7%, 61.1%, 41.1% and 20.7% of 4 micron beads coated with gp41 antigen. In these experiments a histogram peak was observed which moved to the left on the X-axis as dilutions were increased such that the fluorescence intensity decreased from 890 to 763 to 613 to 458 to 102 respectively with the dilution factors listed above. Irrespective of the fluorescence intensity of these families of peaks the peak areas expressed as a % of the total events acquired was observed to be 75.1%, 57.7%, 40.5%, and 22.1% with respect to the gp41 coated bead proportions listed above.

EXAMPLE 3

1. THE SUMMED AREA OF OVERLAPPING PEAKS IS DETERMINED BY THE PROPORTIONALITY OF THE REAGENT BEADS WHOSE FLUORESCENCE CONTRIBUTES TO THE COMBINED PEAK IN THE HISTOGRAM.

2. THE AREA OF A HISTOGRAM PEAK ARISING FROM NONSPECIFIC BINDING, I.E. A NEGATIVE, IS DETERMINED BY THE PROPORTIONALITY OF THE RESPECTIVE BEADS IN THE REAGENT.

Using the methods described above it was observed that the histogram peaks of two sera each positive for a different antibody can exhibit the same or nearly the same fluorescence intensity value. Thus it is possible that a serum positive for two analytes might exhibit one peak, i.e. an overlapping peak or partially overlapping peaks. Proportional bead reagents were prepared which contained 4 micron beads coated with HIV antigen gp41, IgG, or HIV antigen p24. A first set of reagents was prepared which contained 20% of p24 coated beads in which the proportion of either gp41 or IgG coated beads was 80% (within procedural error). These two reagents were each contacted with a serum positive for gp41 and IgG but negative for p24. In this first instance two peaks were observed in each of the two histograms, one in the left hand,region (mcf 372) of the histogram of area 23% indicating a negative p24 result and one further to the right. The right most peaks in these cases each had an area of 76% of total counted events and both exhibited mean channel fluorescence values of 624 and 628 respectively indicating the potential for overlapping peaks had both p41 and IgG coated beads been included in the reagent.

A second set of reagents was prepared wherein the proportion of p24 beads was 17.7% of the total (within procedural error). In this reagent set beads coated with gp41 or IgG were both added to comprise 82.3% of the total number of beads wherein each was added reciprocally in varying amounts from 0% to 82.3% to make a set of 5 reagents each with a different IgG and gp41 proportion. These reagents were contacted with the serum above which was p24 negative, IgG and gp41 positive and in which the IgG and gp41 derived peaks were expected to overlap. The observed patterns in each of these five cases revealed a left most peak of mean mcf value 366 and an average area of 23.6% of the total events indicative of the p24 negative status of the serum. A second, right hand singlicate peak of mean mcf 621 was also observed in all 5 cases with an average area of 76.4% indicating a consistent sum for the combination of gp41 and IgG irrespective of their individual bead proportions.

Another set of 5 three bead reagents were prepared wherein the proportion of p24 coated beads was 77.6% and the gp41 and IgG coated beads were added in varying and reciprocal amounts to total 22.4% (on average, within, procedural error). When these 5 reagents where separately contacted with the same serum as above a pattern like that reported above was observed except that the left hand peak held an area of 79.5% of the total events and the right hand or gp41 and IgG positive peak had an average area of 20.5% of the total events.

EXAMPLE 4

UNIQUE BEAD REAGENT PROPORTIONS

It is known that serum can be positive for many different antibodies as for example in a blood bank infectious disease screen. Since the MCF of a positive histogram peak may drift with the particular antibody titer it is possible that several positive peaks could overlap when using an immunoreactive bead assay as described here. To perform a discrete analysis proportional reagents are prepared in such a way as to cause every possible combination of overlapping histogram peaks to have a unique area. A three part reagent for example could be prepared in the proportions 1:2:4 because all possible integer combinations of 1, 2 and 4 are unique. The proportional reagent in this case would contain 14.3%, 28.6% and 57.1% each of the three bead types and seven distinctive histogram peaks are possible with the following percentages of the total beads counted: 14.3%, 28.6%, 42.9%, 57.1%, 71.4%, 85.7% and 100%. The presence of one or more of these peaks is uniquely predictive of which analytes are present in the sample.

EXAMPLE 5

NON-UNIQUE REAGENT PROPORTIONS

Reagents are devised wherein the proportions of beads are not uniquely determined such that nondiscrete analysis is performed wherein the presence of one or more of a class of analytes is determined but the particular analyte cannot be identified. Reagents are also configured to perform discrete analysis of some analytes and nondiscrete analysis of others.

EXAMPLE 6

HETEROGENOUS BEAD SIZE REAGENTS

Proportional reagents are prepared wherein not all the beads are the same size. The forward scatter trigger is set so as to include as counted events all the different size beads employed. Such a heterogeneous proportional reagent exhibits the same features as have been described in examples one through five above.

Using the methods described above it is noted that the MCF of a given positive serum is increased if the analysis is performed using a larger bead in the second instance than in the first case. Reagents can be purposefully configured to avoid the overlap of histogram peaks by coating one of the analyte binding complement on a bead larger than the others.

EXAMPLE 7

GATED MULTIPLEX REAGENT ANALYSIS

Proportional reagents are prepared wherein beads of two or more size classes are mixed. Each bead size class is coated as described above and blended in predetermined proportions. The coated bead size classes each proportionately blended are then added together to form a reagent containing all the various bead size subpopulations. The assay and analysis is performed as previously described in an apparatus of the type shown in FIG. 4 except that the histogram for each bead size subclass is analyzed using the "gating" technique described by Fulwyler, McHugh and others. Each histogram when analyzed individually exhibits the unique peak area distributions as have been described in example one through five above. Accordingly a number of discrete assays can be performed on one bead size simultaneously with a second number of assays performed on a second bead size and so on.

EXAMPLE 8

FLUORESCENCE TRIGGERING

In the previous examples the functionality of forward scatter in an apparatus as depicted in FIG. 4 was utilized to acquire a preselected number of events into the fluorescence intensity data set. In those cases a trigger or threshold was set to select as countable events only those beads passing through the flowcell of a certain minimum size, for example 2 microns diameter. An advantageous analysis was done whereby forward scatter was not utilized as the event trigger but fluorescence intensity above a certain preselected value was used to acquire events into the data set. One advantage of this method of analysis was that none of the functions, optics or electronics of forward scatter or side scatter was necessary.

An experiment of design as in example one above was performed wherein 4 micron beads were counted with either HIV antigen gp41 or antihuman IgG. Proportional reagents were prepared in which the gp41 coated beads comprised 100%, 89%, 79%, 69%, 58%, 48%, 38%, 29%, 19%, 9% and 0% of the total beads respectively and the IgG coated beads made up the balance in the reagents. These reagents were contacted with serum known to be positive for both IgG and gp41 antibody. The completed reaction mixture was delivered to a FACScan flow cytometer (Becton Dickinson) of design as depicted in FIG. 4. The analysis was performed in three ways: 1) triggering was set on forward scatter at a threshold value of 348 to exclude particles of less than 2 micron from acquisition into the data set, and 2) triggering was set on fluorescence intensity at FL1 settings of 400 or 450 to exclude from acquisition into the data set varying degrees of the low intensity fluorescence noise coming from fluorescent debris of ubiquitous origins.

Inspection of the histograms derived from each of the experiments above revealed two peaks (except in the case of 0% bead proportion): one of average mcf of 517 and a second of average mcf 725 indicating the positive presence in the serum of both IgG and gp41 antibody. These peaks were non overlapping in all cases. A marker was set between the two peaks by inspection of the first histogram printed out and this setting was used throughout the rest of the histograms. The total number of events on each side of the marker, i.e. the area of each peak, was recorded and was enumerated as a percent of the total events acquired.

The peak areas of the rightmost peak (gp41, deduced as follows by the coincidence of reagent proportion and peak area) in the forward scatter triggered evaluations were 89%, 80%, 70%, 60%, 50%, 43%, 33%, 17%, 8%, and 0%. The coefficient of correlation (r ,squared) of these data with the respective gp41 coated bead proportions listed above was 0.9928. The peak areas of the rightmost peaks in the fluorescent trigger of 400 experiments were 87%, 77%, 68%, 62%, 54%, 45%, 34%, 26%, 17%, 9.5%, and 3% to yield a coefficient of correlation of 0.9982 with the bead reagent proportions as above. Fluorescence triggering atia threshold of 450 yielded nearly identical results with a 0.9952 correlation coefficient. A similar numerical analysis for the left most peak in the histograms (IgG by deduction) yielded the expected reciprocal numbers and high coefficients of correlation. Analysis of covariability indicated that much of the lack of absolute correlation could be accounted for by subjective error in the placement of the marker separating the peaks.

These results indicate that the tautology of preselected proportionality of reagent beads coated with a specific member of a binding pair with the area of the resultant histogram peak holds whether forward scatter (i.e., bead size discrimination) triggering or fluorescence intensity triggering is employed to define the total number and type of events collected into the data set. Thus it is not necessary for purposes of these analyses to employ or even have present in the flow cytometer the devices (detectors, lenses, and electronics) required for other applications of the flow cytometer. Thus an apparatus devoid of these devices as depicted in FIG. 5 could be employed with good result.

EXAMPLE 9

A FOUR ANALYTE HIV ASSAY

Using the methods described above and utilizing forward scatter as a trigger an analysis of known positive serum was performed using 4 micron polystyrene beads coated with antigens IgG, HIV gp41, HIV p24, and hepatitis 1B core protein (HBc) in the proportions 13%, 53%, 27% and 7% respectively. The resultant histogram of a known serum positive for all four antibodies had four peaks, each of unique size as follows wherein 5000 total events were plotted: 663 events (13% mcf 640), 2522 events (50% mcf 731), 1406 events (28% mcf 822), and 324 events (6.5% mcf 421) respectively. Other sera which were negative or positive for One or more of the antibodies each exhibited unique peak patterns which allowed the correct qualitative interpretation of the serum reactivity.

The present invention includes the capability to perform qualitative, semi-quantitative, and quantitative assays. Qualitative assays (presence/absence) are encompassed by the invention wherein the simple presence of a histogram peak of mcf value above background (nonspecific binding) indicates the presence of analyte in the sample wherein the area of that histogram peak specifically identifies the analyte from a number of possible analytes as predetermined by the composition of the reagent. Semiquantitative assays (presence in the sample of analyte above a predetermined quantity or indirect measure of that quantity) are encompassed wherein the presence of a histogram peak above a certain predetermined mcf value (cut-off or discriminator) indicates the presence of the analyte in the sample at a concentration above a meaningful minimum and wherein the area of that histogram peak specifically identifies the analyte from a number of analytes as above. Using a similar identification logic quantitative assays are described where the known concentration of the analyte(s) of interest as determined by other methods is related to a standard curve of fluorescence intensity such that the mcf value of the histogram curve are analytically related to concentration of analyte in the sample. These heretofore mentioned methods refer to discrete assays in which the analytes are specifically identified by the method utilizing the tautology of coated bead proportionality in the reagent with the area of the histogram peak. When these unique proportions are not employed in the reagent a nondiscrete assay technology is derived wherein the presence or absence of one or more of the subject analytes can be stated but the analyte or analytes cannot be specifically identified.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for simultaneously detecting multiple analytes of interest in a sample, said method comprising:

(a) combining said sample with a composition comprising a population of particulate supports that are detectable by flow cytometry techniques, wherein A. each particulate support consists essentially of an unlabeled particle to which is bound exactly one of a set of at least two unlabeled specific reagents, each of said specific reagents is capable of binding specifically to one of the multiple analytes of interest, B. the population comprises discrete subpopulations of supports, each of which consists of those supports comprising the same specific reagent, wherein the combined number of supports in any two or more subpopulations is unique as compared to the number of supports in any other combination of subpopulations or as to a single subpopulation, C. each subpopulation constitutes a predetermined, known proportion of the population of particulate supports, and D. the particles of the population are substantially physically indistinguishable from each other, the particulate supports being of approximately the same mean diameter, whereby in the presence of one or more analytes a discrete population of specific binding pars is formed on the supports of each subpopulation for each analyte of interest in the sample;

(b) contacting said specific binding parts with a labeled agent, said labeled agent comprising a number of specific binding moieties each attached to a fluorochrome which emits a detectable fluorescence upon exposure to excitation energy, wherein each of the binding moieties is specific for one of the multiple analytes and the same fluorochrome is attached to each of the binding moieties;

(c) removing any unbound labeled agent and detecting fluorescence intensity of each particulate support of a preselected number of said population of particulate supports using flow cytometry techniques;

(d) obtaining a histogram plot of said preselected number of particulate supports detected as a function of the logarithm of said fluorescence intensity detected, said histogram plot contains one or more peaks, wherein each peak has an area which indicates the proportion of each subpopulation of particulate supports of said preselected number associated with said peak, and wherein each peak has a position for each analyte detected which may be the same as or different from the peak position of any other analyte detected and wherein absence of one or more analytes results in a peak having a position at essentially background fluorescence; and (e) identifying analytes present in said simple by the relative proportion of each peak as a function of the relative proportion of said preselected supports.

2. The method according to claim 1, wherein said multiple discrete subpopulations are from two to four discrete subpopulations.

3. The method according to claim 1, wherein said analyte of interest comprise an antigen or an antibody.

4. The method according to claim 1, wherein said reagents comprise an antigen or an antibody.

5. The method according to claim 1, wherein said composition comprises four discrete subpopulations.

* * * * *